United States Patent [19]

Sato et al.

[11] Patent Number: 4,657,660

[45] Date of Patent: Apr. 14, 1987

[54] APPARATUS FOR SENSING OXYGEN CONCENTRATION

[75] Inventors: Kanemasa Sato; Sadayasu Ueno, both of Katsuta; Norio Ichikawa, Mito, all of Japan

[73] Assignee: Hitachi, Ltd., Tokyo, Japan

[21] Appl. No.: 776,663

[22] Filed: Sep. 16, 1985

[30] Foreign Application Priority Data

Sep. 14, 1984 [JP] Japan .................. 59-193265

[51] Int. Cl.⁴ ............................................ G01N 27/58
[52] U.S. Cl. .................................... 204/427; 204/428; 204/429
[58] Field of Search .................. 204/427, 428, 429, 15

[56] References Cited

U.S. PATENT DOCUMENTS

| 4,283,703 | 8/1981 | Horwitt | 338/34 |
| 4,512,871 | 4/1985 | Kato et al. | 204/429 |
| 4,528,086 | 7/1985 | Kato et al. | 204/427 |
| 4,540,479 | 9/1985 | Sakurai et al. | 204/427 |
| 4,560,463 | 12/1985 | Frey et al. | 204/424 |

Primary Examiner—G. L. Kaplan
Attorney, Agent, or Firm—Antonelli, Terry & Wands

[57] ABSTRACT

Apparatus for sensing oxygen concentration using a solid electrolyte of cylindrical shape, with a heater disposed within the solid electrolyte, is disclosed. The member supporting the heater, and the leads for the heater, are integrally bonded to the heater through an inorganic bonding member such as glass. By integrally bonding the support member and leads through an inorganic bonding member, the heater length can be reduced.

11 Claims, 6 Drawing Figures

APPARATUS FOR SENSING OXYGEN CONCENTRATION

BACKGROUND OF THE INVENTION

The present invention relates to an apparatus for sensing oxygen concentration wherein a solid electrolyte is employed for sensing oxygen concentration, and more particularly, to such an apparatus which is suitable for use in sensing the concentration of the oxygen contained in a combustion gas and thereby properly controlling the mixture ratio of air and fuel according to the running condition of an automobile.

Such apparatus for sensing oxygen concentration (hereafter referred to as an "$O_2$ sensor") is used as a stoichiometric air fuel mixture ratio sensor in which an electromotive force is generated between a reference gas and an exhaust gas which are separated by a partition wall of a solid electrolyte made of, for example, zirconia, and which controls the mixture ratio of air and fuel supplied to an engine in the approximate ratio of 1:4.7.

A system was at one point proposed for improving the accuracy of an $O_2$ sensor in which a cylindrical electrolyte which is closed at one end is kept heated by inserting a bar shaped heater therein, but this resulted in a relatively complicated apparatus requiring three terminals. More recently, there has been a proposal for a so-called lean $O_2$ sensor as, for example, described in Japanese Patent Laid-Open No. 100746/1983. In this lean $O_2$ sensor, a diffusion layer of 400 $\mu$m to 500 $\mu$m is formed on a cathode and a current of oxygen ions is forcefully pumped in an electrolyte between the cathode and the anode. This current is employed as a medium for sensing the degree of concentration of oxygen of the gas of concern relative to a reference gas. Such a lean $O_2$ sensor requires at least four terminals. Two of these are required for a heater. The other two are necessary for supplying a current of oxygen ions since the cathode of the leads connecting to these terminals cannot be grounded because of the voltage drop which would occur if the cathode were grounded. In an $O_2$ sensor of the above mentioned types including the lean $O_2$ sensor, the electrode extending portion for a heater is Ni plated and the lead wires of nickel are secured by a silver solder. The secured portion by the silver solder, however, is oxidatively corroded in an oxidizing atmosphere, disadvantageously causing a natural separation to occur. It is known that, when a heater is included in the lean $O_2$ sensor assembly and the sensor is mounted on the exhaust pipe of an automobile, the plug member of the lean $O_2$ sensor comes to have a surface temperature as high as 500° C. in the summer months when the automobile engine is idling after running at high speed. Therefore, if a sensor is used in such a high temperature oxidizing atmosphere, it is necessary to have a long heater so that the joint of the heater and its leads are separated from the distal end of the plug member to prevent the temperature of the heater lead joint from exceeding 200° C. When a bar heater is made long, the heater includes a bend of, for example, 0.2 to 0.3 mm relative to its length of 50 mm. In this state, if the heater is inserted into the inner bore of a zirconia element, it is offset. This leads to deterioration in the temperature distribution of the element and lowering of the average temperature of the element which in turn results in a deterioration in the flow of oxygen ions and lowering of the output. Further, a long bar heater involves a correspondingly large bend in the assembly operation, disadvantageously increasing the possibility of breakage.

SUMMARY OF THE INVENTION

Accordingly, a primary object of the present invention is to provide an apparatus for sensing oxygen concentration which is small-sized and durable.

To this end, in an apparatus for sensing oxygen concentration according to this invention, one end of a heater which is connected to heater leads is integrally bonded to a supporting member by means of an inorganic bonding member, and the heater is supported at the inner peripheral side of a cylindrical solid electrolyte, which is closed at one end, by means of the supporting member.

An apparatus for sensing oxygen concentration according to the present invention comprises a cylindrical solid electrolyte which is open at one end and closed at the other; a heater arranged at the inner peripheral side of this cylindrical solid electrolyte; a supporting member, arranged at the end of the heater, which is positioned at the open side of the solid electrolyte for supporting the heater at the inner peripheral side of the solid electrolyte; leads connected to the end of the heater which is positioned at the open side of the solid electrolyte for supplying power to the heater; a detecting electrode formed on a part of the solid electrolyte; and outer and an inner lead electrodes for providing an output from the detecting electrode, wherein the supporting member and the leads are integrally bonded to the heater by means of an inorganic bonding member.

According to one preferred embodiment of this invention, the heater is supported by the supporting member in such a manner that a reference gas inlet passage is formed between the solid electrolyte and the heater and the supporting member is provided with an opening which is communicated with the reference gas inlet passage. The inorganic bonding member is comprised of glass.

In the apparatus of sensing oxygen concentration according to this invention, it is possible for the length of a heater to be reduced, and, as a result, the overall size of the heater is made smaller and the durability increased.

The above and other objects, features and advantages of the present invention will become more apparent from the following description of the preferred embodiment thereof, taken in conjunction with the accompanying drawings.

DETAILED DESCRIPTION OF THE PREFERRED EMBODIMENT

An embodiment of the present invention will be described hereinunder in detail with reference to the accompanying drawings.

Figure 3:
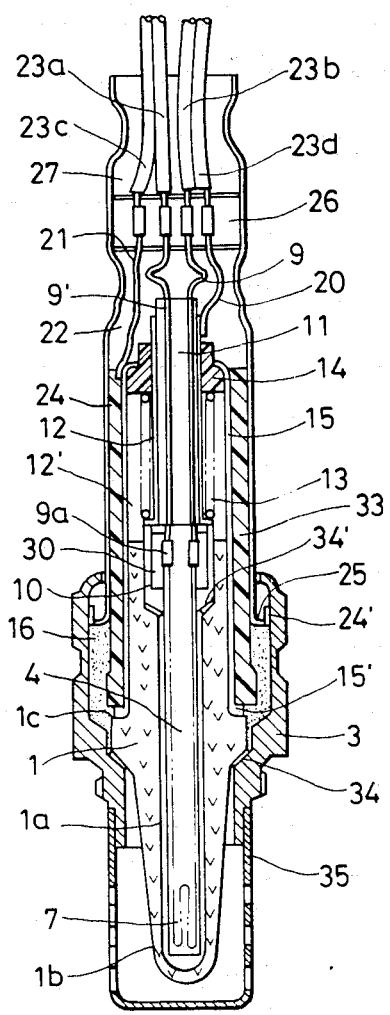
FIG. 3 shows the structure of one embodiment of an lean $O_2$ sensor incorporating the heater according to this invention.

As shown in FIG. 3, a cylindrical solid electrolyte element 1 which is closed at one end is made of, for example, zirconia and has a shoulder on the side of its inner periphery by which the inner periphery is divided into a smaller and larger inner diameter portions. The smaller diameter portion of the inner wall surface is coated with platinum toward the distal end of the electrolyte element 1 to form a porous electrode 1a. This electrode 1a is led as far as the shoulder on the inner wall surface which constitutes the position where the diameter becomes larger. On the other hand, a porous detecting electrode 1b is formed on the outer peripheral side of the element 1 covering the distal end of the element 1. A lead of the detecting electrode 1b is led upward as high as the upper side of the element 1. The outer detecting electrode 1b is coated with a protective film (not shown) of magnesia spinel by plasma spray coating. The protective film has a thickness of about 400 to 500 μm and acts to limit difussion of oxygen. In addition, a lead portion of the platinum electrode is also coated with a protective film of 50 to 60 μm thickness as high as a flange portion 1c of the element 1 by which the element is fixed to a plug member 3 for the purpose of insulation. A heater assembly 4 is inserted inside the element 1. The heater assembly 4 is positioned therein in such a manner that the maximum temperature portion of the heater effectively heats the outer detecting electrode 1b of the element 1. Leads 9, 9' for the heater extend through an insulating tube 11. A metal pipe 12 having a flange is fitted on the outer periphery of the alumina insulating tube 11. The metal pipe is joined to the platinum electrode formed on the outer periphery of a heater flange 10 at the bottom face of the flange portion of the metal pipe 12 to conduct electricity. Further, a coil spring 13 is fitted to the upper face of the flange portion 12' of the metal pipe 12 such as to support the heater assembly 4 by pressing it against the closed end side of the element 1 through the shoulder thereof which is provided on its inner periphery. The other end of the coil spring 13 contacts an insulator 14 of steatite, which is retained by a metal case 15. The metal case 15 is provided with a flange-like bottom, and is retained by an outer peripheral cover 24 through an insulator 33 of steatite. Alumina powder 16 is pressingly sealed and secured between the plug member 3 and the element 1 via the insulator 33. At this time, the bottom face of the flange of the metal case 15 is electrically connected to the outer electrode 1b of the element 1. A metal packing 34 is inserted between the plug member 3 and the element 1 to maintain a hermetic seal. Similarly, a metal packing 34' is inserted between the heater flange 10 and the shoulder on the inner periphery of the element 1. On the other hand, a protective tube 35 having several gas inlet bores is secured to the plug member 3 on its exhaust side. The other end of the metal pipe 12 is provided with a relaying lead 20 which is welded thereto, while a relaying lead 21 is welded to the other end of the metal case 15. These leads 20, 21 together with the heater leads 9, 9' are respectively connected to insulation coated leads 23a, 23b, 23c and 23d through an insulator 22 and are extended outside. A flange portion 24' provided at the bottom of the outer peripheral cover 24 is pressed against the powder 16 and a metal ring 25 is arranged at the upper face of the flange portion and the upper end of the plug member 3 is caulked onto the surface of the peripheral cover 24 to fix the peripheral cover 24. The upper end of the outer peripheral cover 24 through which the lead wires are extended to the outside is packed with insulators 26, 27 and is caulked. The outer peripheral cover 24 is also similarly caulked at the position of an insulator 22 located below the insulators 26, 27.

Figure 2A:
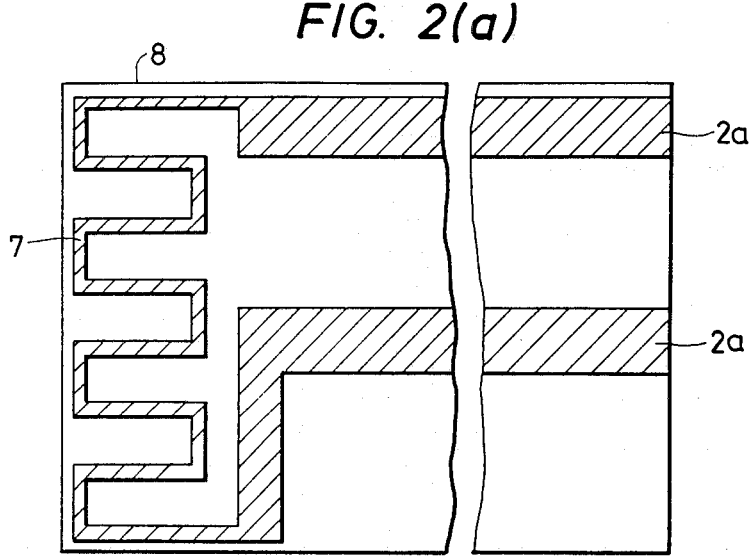
FIG. 2(a) shows a heater pattern printed on an aluminum sheet.
Figure 2B:
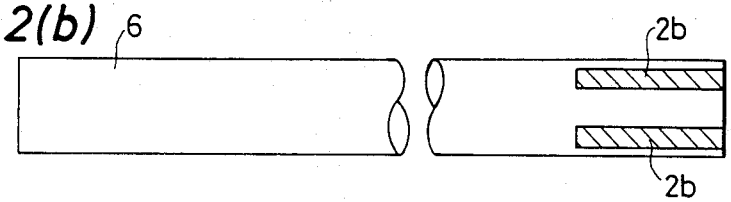
FIG. 2(b) shows a core bar of the heater on which the aluminum sheet is wound.

A heater is constructed, as shown in FIG. 2(b), by winding around the outer periphery of a ceramic core 6 an aluminum sheet 8 having a printed heater pattern 7 of tungsten (shown in FIG. 2 (a)). Extension of the leads is performed by arranging lead extending portions, which are separately printed, at the distal end of the core 6 in such a manner that they lie on lead extending portions 2a of the aluminum sheet 8 when the core 6 is covered with the aluminum sheet 8. The lead portions 2b of tungsten of the heater are Ni plated in advance and the leads 9, 9' are fixed thereto by means of a silver solder 9a. The aluminum flange portion 10 for supporting the heater is separately formed so that it has a hollow therein, and is positioned at one end of the heater in such a manner that it encircles the joint between the leads and the heater 5. A glass powder 30 is filled in the hollow formed in the heater flange which includes the heater leads portion connected to the heater 5, and is baked so as to integrally secure the heater to the heater flange, whereby the heater assembly 4 is constructed. The heater flange 10 is provided with a groove 32 allowing for passage of a reference gas. At the time of glass baking, a part of the flange portion 10 is printed with a platinum electrode lead 31 directed from the bottom face thereof toward the upper face such as to form an inner lead electrode. The lean $O_2$ sensor constructed in this manner is mounted to the exhaust gas pipe (not shown). Then, the heater is subjected to DC 14 V, while the electrolyte is supplied with 0.5 to 0.6 V to cause a pumping current of oxygen ions to flow whereby output of the pumping current is obtained in the range from 1 to 4 mA according to the oxygen concentration of the exhaust gas.

Figure 4:
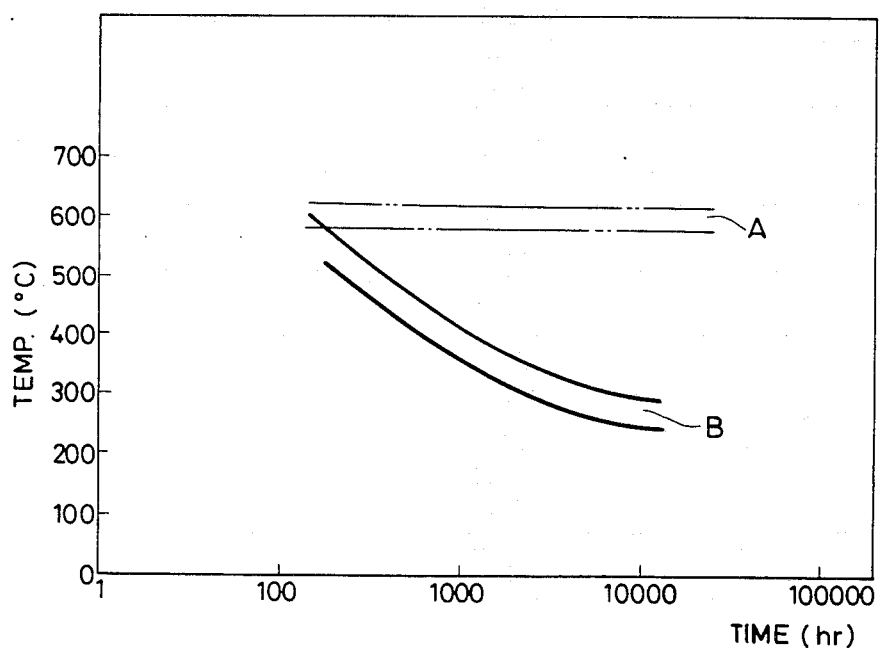
FIG. 4 is a graph of the durability of a joint between a heater and its leads.

In one embodiment of the present invention, the length of the heater is reduced by half or more as compared with the conventional $O_2$ sensor, making the overall size smaller. Furthermore, since the degree of bending of the bar shaped heater is decreased, the temperature distribution of the electrolyte can be made uniform and the output characteristics become stable. The smaller degree of bending of the heater can also lead to better quality control. Because the heater is shorter, it requires less power than conventional heaters, thereby conserving energy. According to this embodiment, the leads extending portion of the heater is covered with the glass and this results in its having improved heat resistance, as shown by symbol A in FIG. 4, in which B denotes that of the conventional example. Hence, durability of the sensor is also increased.

Figure 1A:
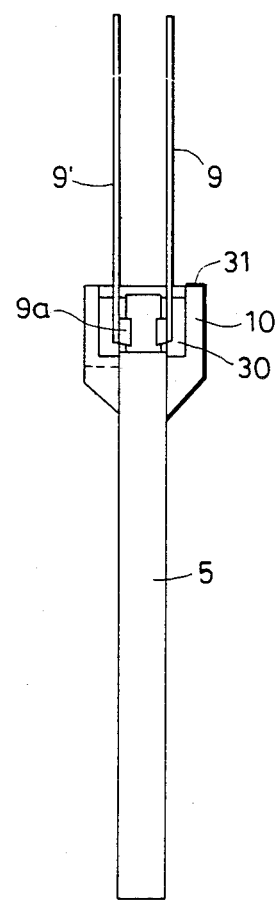
FIGS. 1(a) and 1(b) show one example of the structure of a heater incorporated in the apparatus for sensing oxygen concentration according to the present invention.
Figure 1B:
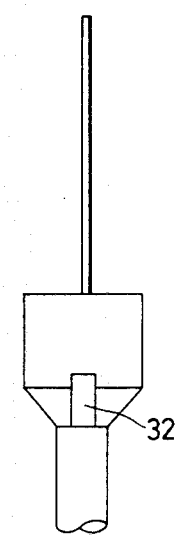

Since a part of the outer periphery of the heater flange 10 is coated with a platinum paste and is pressed against the inner electrode such as to form its lead, the reference gas is led in by providing a notch, as shown by numeral 32 in FIG. 1, advantageously making the heater size small.

What we claim is:

1. An apparatus for sensing oxygen concentration comprising: a cylindrical solid electrolyte which is open at one end and closed at the other end; a heater disposed on the inner peripheral side of said cylindrical solid electrolyte, the heater having an end positioned at the open end of the solid electrolyte; a supporting member disposed at the end of said heater which is positioned at the open end of said solid electrolyte, said supporting member being disposed so as to support said heater on the inner peripheral side of said solid electrolyte; lead members connected to said end of said heater which is positioned at the open end of said solid electrolyte, for supplying power to said heater; detecting electrode means formed on a part of said solid electrolyte; and an outer electrode connection lead means and an inner electrode connection lead means for taking out an output from said detecting electrode means, wherein said supporting member is integrally bonded to said heater by means of an inorganic bonding member.

2. An apparatus for sensing oxygen concentration according to claim 1, wherein said heater is supported by said supporting member in such a manner that a reference gas passage is formed between said solid electrolyte and said heater and said supporting member is provided with an opening which is communicated with said reference gas passage.

3. An apparatus for sensing oxygen concentration according to claim 1, wherein said inorganic bonding member is composed of glass.

4. An apparatus for sensing oxygen concentration according to claim 1, wherein the connection between said lead members and said end of said heater is covered with said inorganic bonding member.

5. An apparatus for sensing oxygen concentration according to claim 4, wherein the lead members are connected to said end of said heater by means of being fixed thereto with a silver solder.

6. An apparatus for sensing oxygen concentration according to claim 1, wherein a hollow is formed between said supporting member and said heater, said hollow being at a location adjacent the connection between said end of said heater and the lead members, and wherein said hollow is filled with said inorganic bonding member so as to integrally bond the supporting member to the heater and to cover the connection between said end of said heater and the lead members.

7. An apparatus for sensing oxygen concentration according to claim 6, wherein the lead members are connected to said end of said heater by means of being fixed thereto with a silver solder.

8. An apparatus for sensing oxygen concentration comprising: a cylindrical solid electrolyte which is open at one end and closed at the other end; a heater disposed at the inner peripheral side of said cylindrical solid electrolyte, the heater having an end positioned at the open end of the solid electrolyte; a supporting member disposed at the end of said heater which is positioned at the open end of said solid electrolyte, said supporting member being disposed so as to support said heater on the inner peripheral side of said solid electrolyte; lead members connected to said end of said heater which is positioned at the open end of said solid electrolyte, for supplying power to said heater; detecting electrode means formed on a part of said solid electrolyte; and an outer electrode connection lead means and an inner electrode connection lead means which are respectively formed on the outer and inner peripheries of said solid electrolyte in such a manner as to extend from said detecting electrode means axially of said solid electrolyte, wherein said supporting member is integrally bonded to said heater by means of an inorganic bonding member.

9. An apparatus for sensing oxygen concentration according to claim 8, wherein the connection between said lead members and said end of said heater is covered with said inorganic bonding member.

10. An apparatus for sensing oxygen concentration comprising: a cylindrical solid electrolyte which is open at one end and closed at the other end; a heater disposed at the inner peripheral side of said cylindrical solid electrolyte, the heater having an end positioned at the open end of the solid electrolyte; a supporting member disposed at the end of said heater which is positioned at the open end of said solid electrolyte, said supporting member being disposed so as to support said heater on the inner peripheral side of said solid electrolyte; lead members connected to said end of said heater which is positioned at the open end of said solid electrolyte, for supplying power to said heater; detecting electrode means formed on a part of said solid electrolyte; an outer electrode connection lead means which is formed on the outer periphery of said solid electrolyte in such a manner as to extend from said detecting electrode means axially of said solid electrolyte; and an inner electrode connection lead means formed on the outer periphery of said supporting member, said supporting member being integrally bonded to said heater by means of an inorganic bonding member.

11. An apparatus for sensing oxygen concentration according to claim 10, wherein the connection between said lead members and said end of said heater is covered with said inorganic bonding member.

* * * * *